United States Patent
Maltin (12) 
(10) Patent No.: US 6,257,751 B1
(45) Date of Patent: Jul. 10, 2001

(54) METHOD AND APPARATUS FOR MAINTAINING SOLIDS IN SUSPENSION IN A LIQUID

(76) Inventor: Christopher Maltin, Gould's House, Horsington, Somerset (GB), BA8 0EW ( * ) Notice: Subject to any disclaimer, the term of this patent is extended or adjusted under 35 U.S.C. 154(b) by 0 days.

(21) Appl. No.: 09/043,286

(22) PCT Filed: Sep. 24, 1996

(86) PCT No.: PCT/GB96/02336

§ 371 Date: Mar. 23, 1998

§ 102(e) Date: Mar. 23, 1998

(87) PCT Pub. No.: WO97/11915

PCT Pub. Date: Apr. 3, 1997

(30) Foreign Application Priority Data

Sep. 25, 1995 (GB) .................................................. 9519499

(51) Int. Cl.[7] .................................................. B01F 13/02
(52) U.S. Cl. .................................................. 366/101; 261/124
(58) Field of Search .................................................. 366/101, 106, 366/107; 261/124; 222/195; 210/197, 220, 221.2

(56) References Cited

U.S. PATENT DOCUMENTS

| | | | |
|---|---|---|---|
| 2,187,466 | * | 1/1940 | Stratford . |
| 2,212,841 | * | 8/1940 | Maxwell . |
| 2,224,741 | * | 12/1940 | Metrick et al. . |
| 2,521,334 | * | 9/1950 | Boerstra .................................................. 366/101 |
| 2,583,725 | * | 1/1952 | Brown et al. .................................................. 366/101 |
| 3,517,732 | * | 6/1970 | Brebant .................................................. 366/101 |
| 3,525,685 | * | 8/1970 | Edwards . |
| 3,810,604 | * | 5/1974 | Reiter .................................................. 366/101 |
| 3,898,162 | | 8/1975 | Carlson et al. . |
| 4,111,808 | | 9/1978 | Fair . |
| 4,142,975 | | 3/1979 | Kinzer . |
| 4,179,375 | * | 12/1979 | Smith .................................................. 210/197 |
| 5,409,610 | | 4/1995 | Clark . |
| 5,470,149 | * | 11/1995 | Witkowski et al. .................................................. 261/124 |

FOREIGN PATENT DOCUMENTS

| | | |
|---|---|---|
| 32 03 386 A1 | 8/1983 | (DE) . |
| 0 120 188 A1 | 10/1984 | (EP) . |
| 0 356 879 A1 | 3/1990 | (EP) . |
| 804249 | 11/1958 | (GB) . |
| 2 178 022 | 2/1987 | (GB) . |

* cited by examiner

*Primary Examiner*—Charles E. Cooley
(74) *Attorney, Agent, or Firm*—Gifford, Krass, Groh, Sprinkle, Anderson & Citkowski, P.C.

(57) ABSTRACT

Apparatus for use in a variety of processes especially those involving bacterial activity such as slurry digestion comprises an elongate stationary container (10) having a cardioid cross-section with an upstanding partial partition (16) projecting upwardly from a lower region and providing a linear array of outlets (15) for the introduction of gas bubbles to the interior of the container. The cardioid container wall comprises a continuous double-lobed curve from an upper region (19) having gas escape outlets (17) to a lower region where the wall curves into tangential relation with the partial partition (16) A modular array of containers in cascade or parallel connection can be interconnected by pipework with valves, pumps and flow sensors for automatic or programmed operation.

7 Claims, 8 Drawing Sheets

METHOD AND APPARATUS FOR MAINTAINING SOLIDS IN SUSPENSION IN A LIQUID

BACKGROUND OF THE INVENTION

The present invention relates to a method for maintaining solids in suspension in a liquid and to a container for use in the method. One example of application of the present invention lies in its potential use in slurry-fermentation processes in which organic or other slurries, such as animal or other wastes are caused, or allowed, to react to produce for example methane and a residue which may be used as a fertilizer and is better for spreading on fields than the original material.

It is known that the fermentation, or digestion, of organic wastes takes place under anaerobic conditions, being caused by anaerobic bacteria in the slurry, and the material must therefore be kept in closed containers for the duration of the fermentation period. This is a relatively long period, which may be of the order of several weeks, during which solids tend to come out of suspension if the slurry is not kept continuously agitated. This can cause various problems, not the least being difficulties in the removal of the solids if, for example, they compact at the bottom of the container or form a floating mass or crust.

DESCRIPTION OF THE PRIOR ART

At present various means are known for keeping the solids in such slurries in suspension, some of which involve mechanical action, such as stirring or the turning of the container itself about an axis to churn its contents. Sometimes gas is bubbled through the slurry to agitate it.

Some of the known methods entail the input of a substantial quantity of energy into the slurry which, in addition to the cost of the equipment itself, militates against the cost-effectiveness of the process as a whole, whilst others are not entirely effective in maintaining the solids in suspension. Digesters are not therefore in such widespread use as might be wished in an age in which fuel economy and recycling of waste products are particularly valued.

SUMMARY OF THE INVENTION

An object of the present invention is, therefore, to provide a method for maintaining solid particles in suspension which can be effected with a smaller input of energy, and therefore at lower cost, than current methods without compromising the effectiveness with which the solids are maintained in suspension. A further object is to provide apparatus for carrying out such a method, which can be manufactured relatively simply and cheaply and is economical to run. A further and, in many respects, more important object is to provide a method and apparatus which will perform reliably over long periods of use to maintain solids of many different types in suspension.

The present invention, in one aspect, provides a method of maintaining solids in suspension in a liquid comprising driving the suspension to follow a circulatory path about a non-vertical axis in a container and constraining the flow to follow the line of minimum energy so as to maintain the solids in suspension.

In another aspect, the invention provides a method of maintaining solids in suspension in a liquid comprising driving the suspension to follow a circulatory path about a non-vertical axis in a container and providing restraint for the flow which forces it to follow a downward curve along at least part of its flow path so as to maintain the solids mixed in suspension in the liquid.

In another aspect, there is provided a slurry container having means for maintaining solids in suspension in a liquid by causing forced circulation thereof with the container stationary, in which part (preferably an upper part) of the container wall is so shaped as to guide the forced fluid flow to follow a curved path with a vertical component so as to maintain the solids in suspension. Alternatively or, more preferably in addition, a lower part of the container wall may be so shaped as to guide the forced fluid flow to follow a curved path with a vertical component so as to maintain the solids in suspension.

It will be appreciated that the method is particularly suitable for maintaining slurries of organic wastes in suspension during fermentation processes and reference will generally be made to this use below but the method is equally applicable to other suspensions.

The method and container of the invention have resulted from the realization that solids and liquids of different specific gravities tend to separate vertically if left stationary but if the liquid and the solids in a slurry are constrained to follow the same path simultaneously, then this relative separating movement will be prevented and the flow will remain substantially uniform or at least more uniform and homogeneous than is achieved in current slurry digesters for the same energy input. Hence the energy input required to achieve a desired degree of homogeneity is reduced.

The energy required to drive the circulatory motion of the slurry can conveniently be provided by the introduction of gas into the lower part of the slurry container, the gas being allowed to bubble up through the slurry and cause the slurry itself, in the vicinity of the gas bubbles, to rise. The gas is allowed to escape at the top of the container while the slurry circulates within it, the movement of the flow being constrained as indicated above, preferably by the shape of the upper part of the container wall, which preferably has a convex curvature towards the interior of the container. The rate of flow of the slurry and the shape of the container wall are preferably such as to achieve substantially laminar flow of the slurry along the wall in use.

In the upper part of its travel the slurry first follows a path with an upward component and a horizontal component directed away from the rising stream of gas bubbles. It is then constrained to move horizontally and downwardly until, eventually, its path becomes substantially vertical. The container may also have a vertical wall component adjacent this region but more preferably the wall is continuously curved so as to direct the flow downwardly and back towards the gas introduction zone.

The gas introduction zone need not be in the lowest part of the container; preferably the container wall is curved to give the flow a downward and horizontal component of movement to the bottom of the container followed by an upward and horizontal component to the gas-introduction zone where the flow becomes substantially vertical. Almost throughout its movement the slurry is thus constrained to follow a curved path, with a smooth flow, that energy is not wasted in creating turbulence and the process may be made more energy-efficient than prior art processes.

The circulatory flow may be driven by gas supplied into a lower or median part of the container. The container could have a circular horizontal section with at least one gas inlet in its base and a domed top but, for simplicity of construction, the container is preferably elongate in a horizontal direction in its position of use and has a uniform cross-section with gas inlets spaced longitudinally thereof. The container may be operated with a batch feed, only one inlet/outlet being provided for the slurry but, more preferably, the container is operated continuously with slurry being fed in and withdrawn through separate inlet and outlet apertures. In this case the slurry is forced to flow longitudinally through the container as well as being subject to the forced circulatory flow.

The gas inlets could be along or adjacent one side of the container but, again for ease of manufacture, it is preferred for the container to be mirror-imaged about a longitudinal plane of symmetry, the gas being introduced along the plane of symmetry so as to set up two circulatory flows in the two halves of the container, one on either side of the plane of symmetry. The two flows are driven in opposite senses by the rising gas stream, in use, with a vertically upward flow in the center of the container which diverges in the upper layers of the liquid into the two halves, each flow being constrained by the shape of the container wall to fall along an outer wall portion and then being directed back to the center along the bottom of the container. Although two flows are set up in the opposite halves, there is preferably an exchange of material between the two halves across the central plane of symmetry so that the entire contents of the container mix homogeneously while they are in the container.

The inlet and outlet for the slurry are preferably in opposite halves of the container and also preferably at opposite ends although they could be at the same end of the container.

As mentioned above, the gas inlets need not be in the lowermost part of the container. In a mirror-imaged container they are preferably located between two curved wall portions forming the bottoms of the two halves, the ends of these wall portions projecting upwardly towards the center of the container where they are interconnected with gas-supply means located between them. The outer ends of the wall portions are preferably interconnected by a wall portion which forms the top of the tank and which forms continuous curves with the lower wall portions. The very top of the container preferably defines a header space in which the gas accumulates before leaving the tank through an upper outlet. The wall portion defining this space may have any configuration but is preferably formed as a continuous curve with the remaining parts of the upper wall such that the container as a whole has a generally cardioid section.

In a further alternative aspect of the invention there is provided a container for slurry or other solid/liquid mixture having an upstanding partition extending from a bottom region thereof to a mid region thereof, the upper wall of the container being formed as a smoothly continuously curved surface such as, in use, to divert an upward flow of fluid in the central region of the container outwards and downwardly in a smooth circulatory movement. In the preferred, elongate form of the container, the partition extends longitudinally of the container and flows are set up in opposite senses in two halves of the container on opposite sides of the plane defined by the partition.

In yet a further aspect of the invention there is provided a container for slurry or other liquid/solid mixture in which the lower boundary of the container is shaped as a curved surface with an intermediate cusp so as, in use, to encourage circulation of the fluid in opposite senses in parts of the container on opposite sides of the cusp.

It will be appreciated that the most preferred form of container has the two features defined above, that is, the smoothly curved top and the cusped bottom. Such a container can conveniently be made from sheet material and another aspect of the invention provides a method of manufacturing a slurry container including the steps of folding opposite edge portions of a rectangular sheet of resiliently flexible material towards each other about parallel fold lines, gripping the edge portions and bending the major portion of the sheet about a plane parallel to the fold lines and in the opposite direction from the folding of the sheet so as to bring the two edge portions close together, the major portion of the sheet forming a continuously-curved container wall, interconnecting the edge portions and fitting end walls to close the open ends of the container wall.

The edge portions are preferably folded so as to lie in contact with one face of the major portion of the sheet before the latter is bent and the sheet is preferably bent until the edge portions are substantially parallel and lie within the overall contour of the container.

A container made in this way has a generally cardioid section, that is, a section which is constituted by two lobes mirror-imaged about a plane of symmetry and interconnected at adjacent ends in the said plane by the two joined edge portions, the opposite ends of the lobes remote from each other also being interconnected, but in this case by a smoothly-curved wall. In use, the container is preferably arranged with the plane of symmetry vertical and the smoothly-curved wall uppermost. Apertures for the inlet of gas for driving a circulation of the suspension in the container are preferably provided between the interconnected edge portions of the sheet.

In use of the container of the invention, a suspension, or slurry, which is to be allowed or caused to react, is supplied into the container which is filled nearly to the top. The suspension or slurry may contain solids in any form, whether as small discrete particles, or granules, flakes or fibres or aggregates of particulate matter, mixtures of different types of solids, both in terms of physical and chemical composition, and solids that are more or less dense than their liquid carrier. Likewise the reaction which is to take place may occur within the suspension itself, being unaffected by the gas or the gas may itself react with the suspension. If the reaction is to be carried out under anaerobic conditions, the container must also be sealed and a suitable gas selected for driving the circulation.

Once the container has been filled with the slurry, gas is then introduced at such a flow rate as to cause the slurry to rise in the center of the container, the flow separating to spread outwards in the two upper parts of the container. The shaping of the container wall is such so as to constrain the suspension to flow downwardly, following its curvature, the solids remaining in suspension in the liquid. It will be understood that the container must be filled to a predetermined high level to enable the two flows to follow the curvature of the upper parts of the container to achieve the flow-enhancement provided by the method of the invention.

As the flows in the two halves of the container continue to fall, they are constrained by the shaping of the lower lobes of the container to follow smoothly curved paths, being returned upwardly to the center of the container where they are again entrained by the upward current of bubbles which thus drives the circulations in the two halves of the container. In the center of the container the two flows can mix to ensure the overall homogeneity of the suspension.

The way in which the apparatus is used permits a number of variations. For example the slurry may be left in the container until reactions within it are complete, it then being replaced by a fresh batch as in current batch digestion procedures. The container of the present invention has the added advantage, however, that it lends itself to use in a continuous process. For this purpose, the slurry may be supplied continuously through an inlet at one end of the container and removed through a separate outlet. The residence time in the digester may be sufficient for digestion to be complete when the slurry is removed, or the partially-digested slurry may be supplied to a further digester or further digesters, in line, to complete the process.

It will be appreciated that it is a particular intention of the invention to minimize the energy that it is needed to introduce into a slurry to keep it in circulation and maintain its homogeneity. The energy input required is minimized by the appropriate shaping of the container wall but, if the desired benefit is to be achieved, the gas flow which drives the circulation must be minimized. The appropriate gas flow rate for a particular container and contents may be calculated or derived experimentally, regulatory means preferably being provided to allow the flow rate to be adjusted to suit different conditions. More preferably, however, monitoring means are provided for monitoring the circulation in the tank and for providing information which enables the gas flow to be adjusted, whether manually or, more preferably, automatically during operation.

The monitoring means are preferably sensors, such as one or more acoustic transducers, which monitor the noise level in the container and, through suitable control means, cause the gas flow to be modulated to maintain the noise level within a predetermined range. Thus the gas flow is increased if the noise level falls below a predetermined threshold, indicating that the movement of the suspension in the container is insufficient to maintain the homogeneity of the suspension, and the gas flow is reduced if the noise level rises above a predetermined threshold indicating that the movement of the suspension is more vigorous than necessary. The gas flow may be adjusted either by changing its flow rate and/or by causing it to be fed intermittently to the container by control of pumps and/or valves for the supply of the gas to the container.

In use of the container as a digester for animal manure, the gas used to drive the circulation must be free from oxygen; nitrogen, carbon dioxide or some other gas which is inert under the conditions of use may be employed. Conveniently, methane from the digestion process itself may be recycled to the container once the process has started.

In use of the container and method of the invention for keeping solids other than animal manure in suspension, gases other than those mentioned above may be used to drive the circulation. In particular, air may be used for suspensions in which aerobic reactions are to take place or in which air has no effect on the constituents.

The container of the invention may be operated in isolation or together with other similar containers, whether interconnected in series or otherwise. In particular, if a container is used for a process involving an exothermic reaction, the heat energy is preferably recovered and utilized so as further to improve the energy-efficiency of the process. For this purpose the container may be housed in an outer container or tank containing a heat-exchange fluid capable of absorbing the reaction heat from the container. In a preferred embodiment of the invention, two or more containers are preferably arranged in a single heat-exchange tank and the heat from an exothermic reaction in one container is transferred via the heat-exchange fluid to the contents of one or more of the other tanks to promote a reaction therein.

BRIEF DESCRIPTION OF THE DRAWING

Several embodiments of the invention will now be more particularly described, by way of example, with reference to the accompanying drawings in which.

Figure 1:
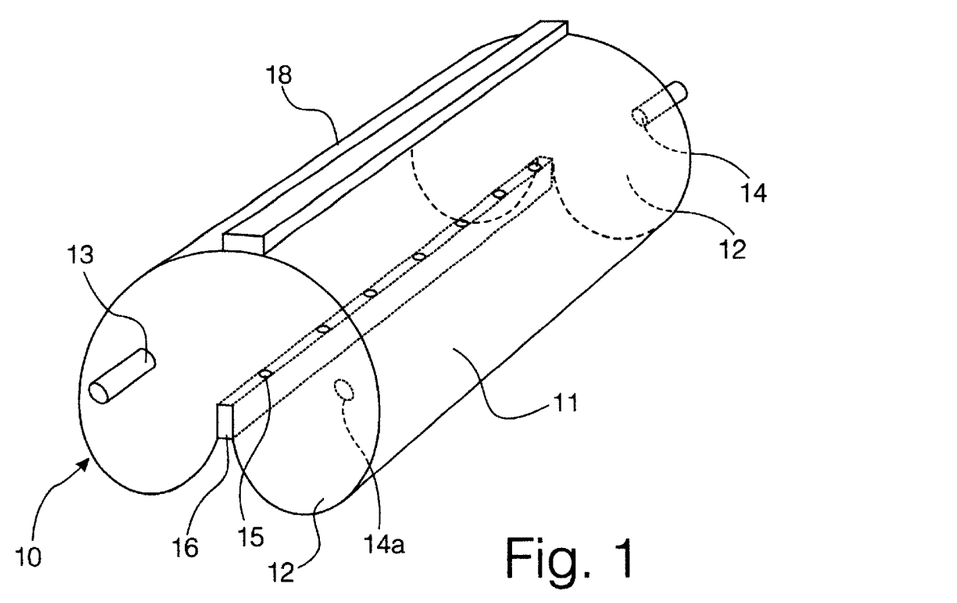
FIG. 1 is a diagrammatic perspective view of a container according to the invention.
Figure 2:
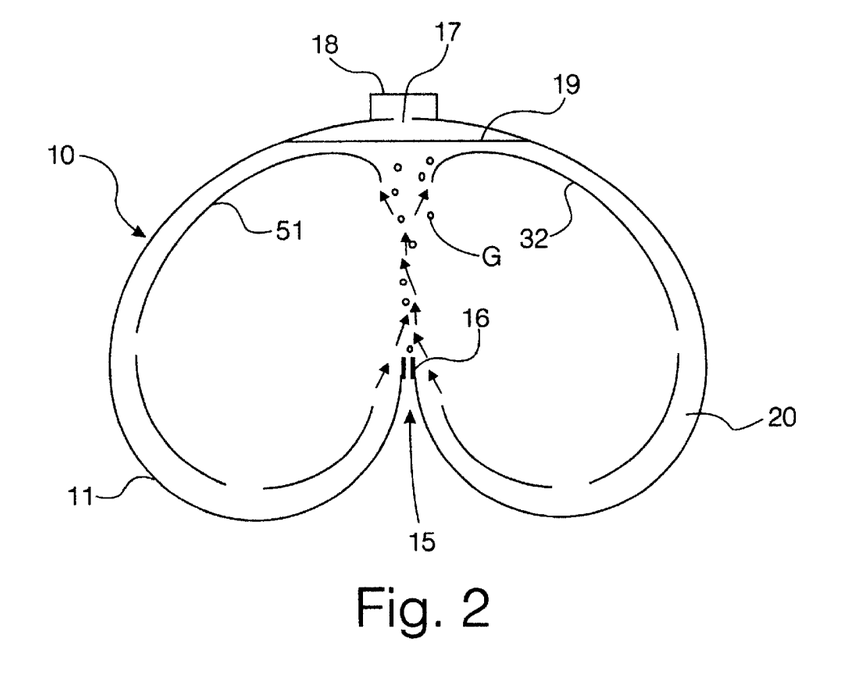
FIG. 2 is a diagrammatic section of the container of FIG. 1.

With reference to FIGS. 1 and 2 of the drawings, a slurry container is generally indicated 10. The container 10 is elongate, with a uniform section defined by a peripheral wall 11, the shape of which will be described more fully below, but which has two lower lobed portions interconnected about a vertical median plane of symmetry of the container. The container also has two flat end walls 12 with the same peripheral shape as the section of the peripheral wall 11 and sealed to the ends to close the container 10.

The opposite end walls 12 each have a closable aperture 13, 14 respectively for the introduction of slurry into the container and its removal therefrom in a continuous process, the two apertures 13, 14 being in opposite halves of the container 10 with respect to its median plane of symmetry. In an alternative embodiment, an outlet aperture 14a is located in the same end wall as the inlet aperture 13 but, again, in the opposite half of the container 10. The positioning of the apertures 13, 14 or 14a is arranged, together with other features of the tank, to ensure that the slurry flows through the container without the creation of stagnant regions. Alternatively the container may have a combined inlet/outlet aperture or may have apertures in its peripheral wall for use of the container in a batch process. Details of such apertures and associated closures or valves are not shown since they are generally known in the art.

The container 10 further includes a plurality of gas inlet apertures 15. These gas inlets 15 are formed in a spacer bar 16 which extends longitudinally of the container 10, in the central median plane of the container, between two edge portions of the peripheral wall 11 which are bent inwardly of the container 10 and sealed to the spacer bar 16. The container also has a plurality of gas outlets 17 in the uppermost part of the peripheral wall which open into a common manifold 18 fixed to the top of the container 10. The gas inlet apertures may also be supplied through a common manifold, not shown.

The apparatus of FIGS. 1 and 2 may further include sensor and regulating equipment, not shown.

In use of the container 10, a slurry 20 of, for example, a mixture of liquid and solid organic waste is fed into the container 10 through the inlet aperture 13 until it reaches the level indicated by the line 19 in FIG. 2 and a gas inert to the slurry is fed through the gas inlets 15. In use with organic wastes, the gas is preferably methane.

As the gas rises, as indicated by gas bubbles G, through the slurry it drives an upward movement of the slurry in the region of the central median plane of the container. From the top of this central region, the slurry then flows in opposite directions towards the peripheral wall which is so shaped as to direct the flows downwardly to the bottom portions of the container where the wall curvature, returning upwardly, also returns the flows upwardly back to the central region of the container. Thus two circulatory flows are set up in opposite senses in the two halves of the container 10, these being indicated S1 and S2, the two flows converging and mixing in the central region. Thus there is exchange of material between the two halves and the entirety of the flow fed in through inlet 13 in one half in due course exits through the outlet 14 in the other half.

During passage through the container 10, the solids in the slurry which, in an animal manure, would tend to float to the surface, are kept mixed with the liquid by the movement. Similarly, heavier particles in a different type of slurry, which would tend to sediment out, would be maintained in suspension.

In this example the slurry is supplied to the container 10 at such a rate that approximately 5% of the container volume passes through every day. In its passage through the container 10 the slurry is subjected to anaerobic digestion, with the evolution of methane which is collected from the manifold 18 together with the inlet gas. If the slurry withdrawn through the outlet 14 is not fully digested it may be passed to one or more further, similar digesters to complete the process.

The flow of slurry through the container 10 may be controlled by suitable pumps and/or valves (not shown) at the inlet 13 and outlet 14, as may the flow of gas through the gas inlet 15, the equipment being controllable manually or automatically. In the latter case in particular, the slurry flow within the container 10 may be monitored by suitable sensors and the results used to control the inflow of gas to regulate it to the minimum required to maintain the circulatory flows S1 and S2 within the container 10. The gas flow may be minimized either by maintaining a constant gas flow at a low rate or by supplying the gas intermittently at a higher rate, whichever is the most energy efficient for a given installation.

In one embodiment of an automatically controlled installation which will be described in more detail in relation to FIG. 8, the or each flow sensor used is an acoustic transducer which monitors the sound produced by the moving slurry in the container 10. An electronic processor is connected to receive signals from the sensor or sensors and to control the pumping, valving and other equipment to maintain the sensor signal within a predetermined range.

The final products from the treatment of slurry in one or more of the containers 10 are the gas withdrawn from the manifold 18 and the mixture of solids and liquids withdrawn from the outlet 14. Some of the gas may be recycled to the gas inlet 15 while, in the case of methane, any excesses may be used as a fuel, for example for electricity generation. The slurry, on the other hand, may be separated into its solid and liquid components both of which, in the case of organic waste, may be usable as fertilizers, possibly after further treatment. The solids may, for example, require composting whilst the liquids may require chelation.

Figure 3:
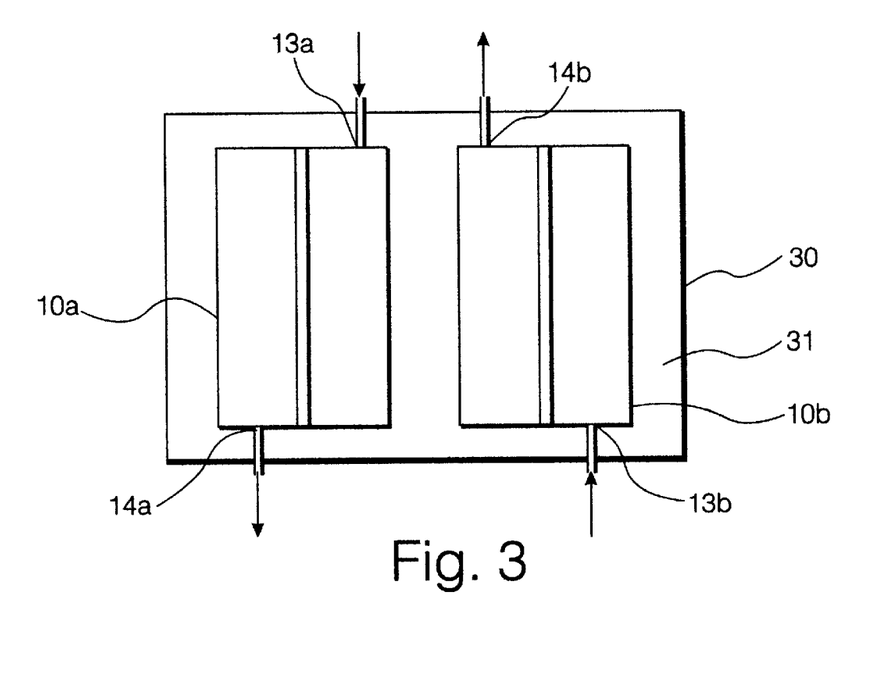
FIG. 3 is a diagrammatic plan view of two of the containers of FIG. 1 used in heat-exchange apparatus.

The basic use of the container 10 for slurry digestion has been described above with reference to FIGS. 1 and 2. Reference will now be made to FIG. 3 which shows two containers 10 in use in heat-exchange apparatus.

In FIG. 3, the two containers, indicated 10a and 10b, are shown side by side in a larger rectangular tank 30 filled with a suitable heat-transfer fluid 31.

The two containers 10a, 10b are shown arranged with their respective inlets 13a, 13b at opposite sides of the tank 30 such that the slurry flows through the containers 10a, 10b in opposite directions across the tank 30 although the containers 10a, 10b could be arranged differently and more than two containers 10 could be employed in a single heat-exchange tank 30.

In use of the apparatus of FIG. 3, a slurry which undergoes an exothermic reaction is supplied to one of the tanks 10a, 10b. The heat from this reaction is transferred through the tank wall to the heat-transfer medium 31 and from there to the other container which is supplied with a slurry which requires heat for its reaction.

In the simplest case, a first slurry which undergoes an exothermic reaction is supplied to one container 10a while a second slurry which undergoes an endothermic reaction is fed to the other container 10b so that the heat required for the endothermic reaction can be supplied extremely efficiently by transfer from the exothermic reaction. Alternatively the slurry supplied to the second container 10b may simply require heat to start its reaction which, once started, is exothermic. In this case the slurry supplied to the first container 10a may simply be taken from the second container 10b once the reaction has been initiated, the outlet 14b of the second container 10b being connected directly to the inlet 13a of the first container 10a. Connecting pipework is in this case preferably arranged in the tank 30.

With reference now to FIGS. 4a–4d of the drawings, these show, purely schematically, steps in the construction of the peripheral wall 11 of the tank 10.

Figure 4A:
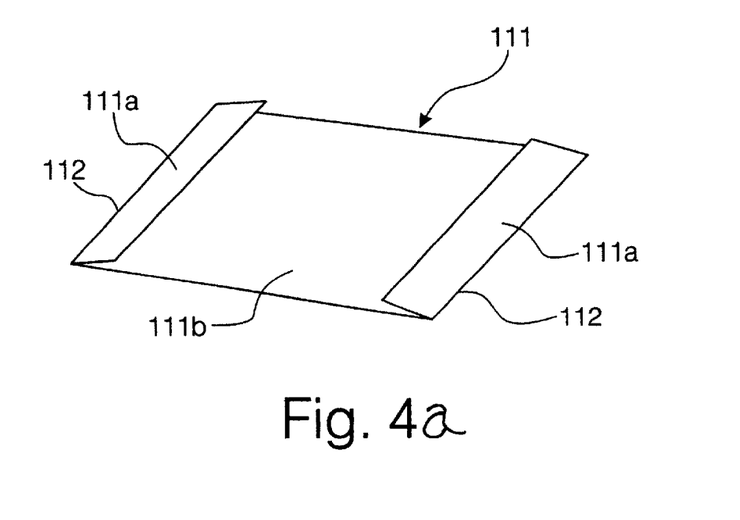
FIGS. 4a–4d are diagrammatic views showing steps in the construction of the container of FIG. 1, FIG. 4a being a perspective view and FIGS. 4b, 4c and 4d being cross-sectional views.
Figure 4B:
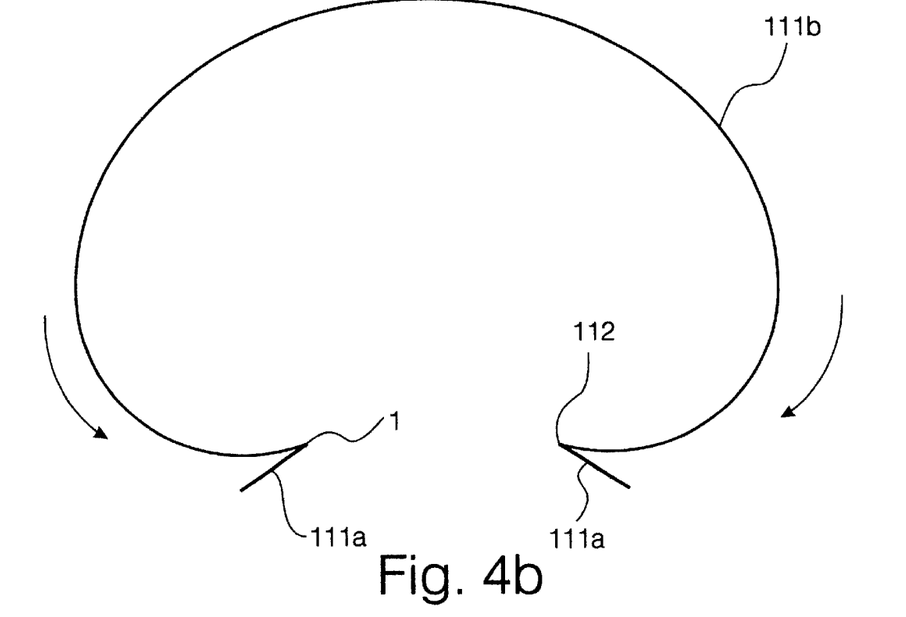
Figure 4C:
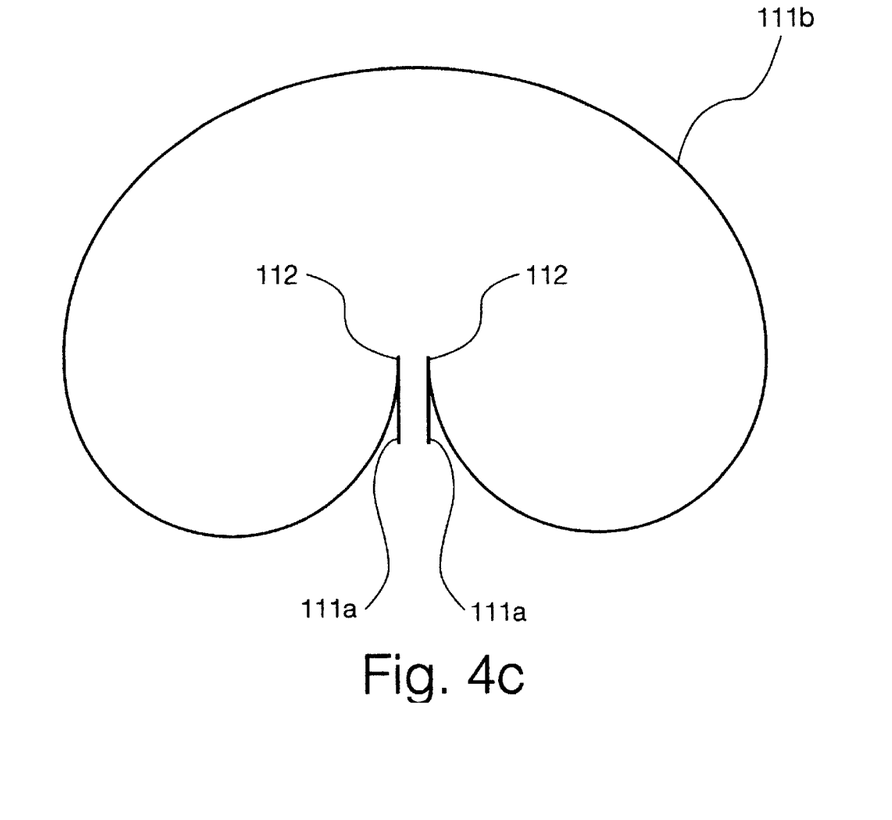
Figure 4D:
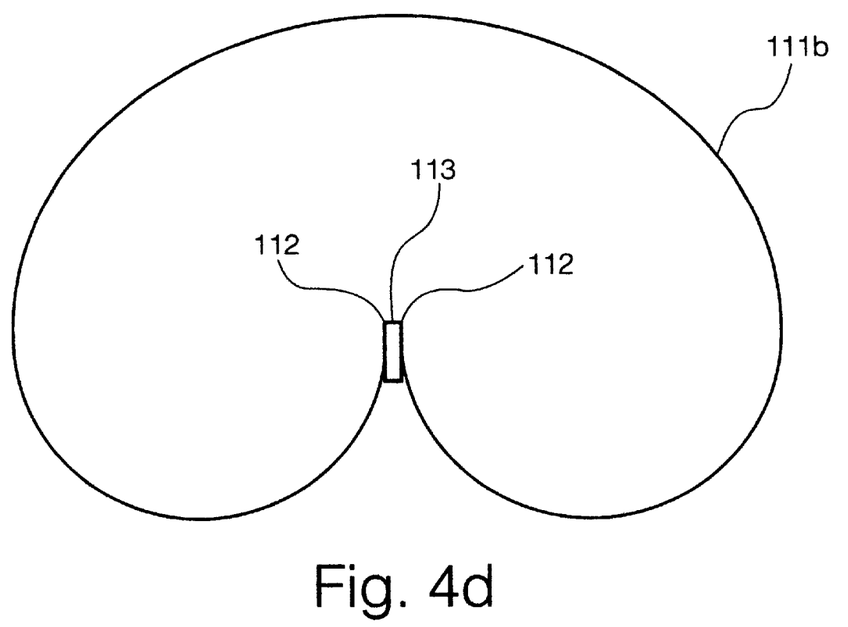

The wall 11 is formed from a flat rectangular sheet of material 111 which may, for example, be of metal or plastics. Two equal, opposite edge portions 111a of the sheet 111 are first folded towards each other about parallel fold lines 112, as shown in FIG. 4a. The two free edges of the portions 111a are then gripped by suitable tools and the main panel 111b of the sheet 111 is bent in a continuous curve about its axis parallel to the fold lines 112 in the opposite direction from the edge portions 111a. In this bending, the sheet 111 passes through the configuration, shown in FIG. 4b to that shown in FIG. 4c in which the edge portions 111a are substantially parallel to and adjacent each other with the fold lines 112 inside the curved shape defined by the panel 111b. Finally, as shown in FIG. 4d, the edge portions 111a adjacent the fold lines 112 are welded or otherwise sealed to a spacer bar 113 which is interposed between them. The edge portions 111a may, of course, be brought together directly onto the spacer bar 113 rather than this being inserted in a separate step. The gas inlet apertures 15 may be formed in any convenient way in the spacer bar 113 before, during or after its sealing between the edge portions 111a.

Figure 5:
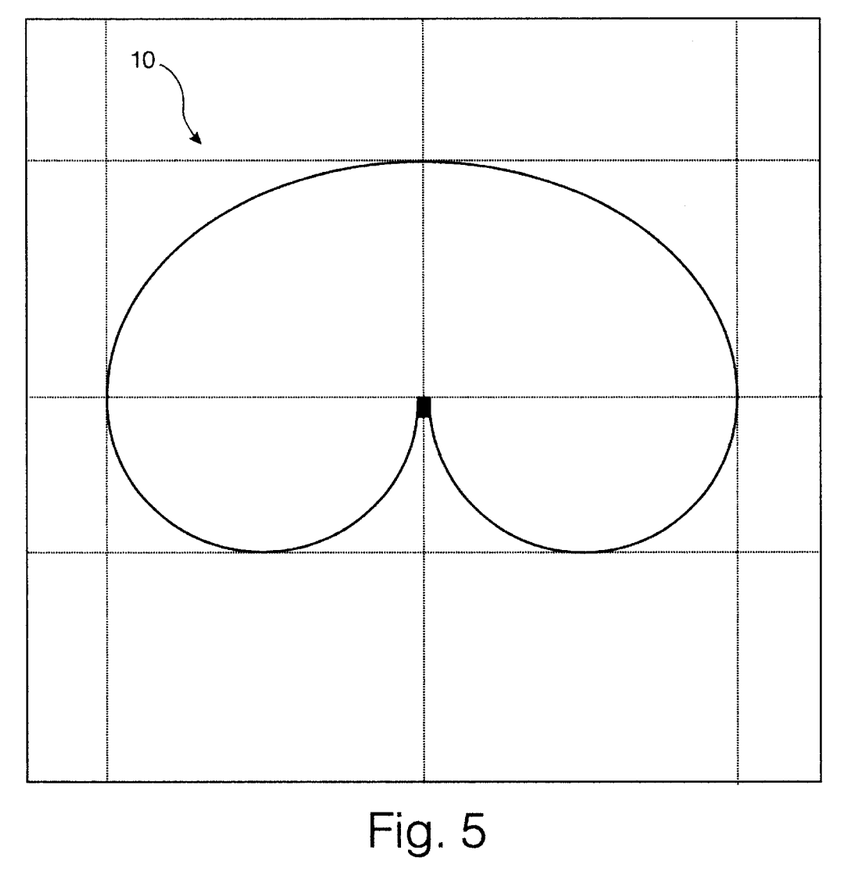
FIG. 5 is a graphical representation of the cross-section of FIG. 2.
Figure 6:
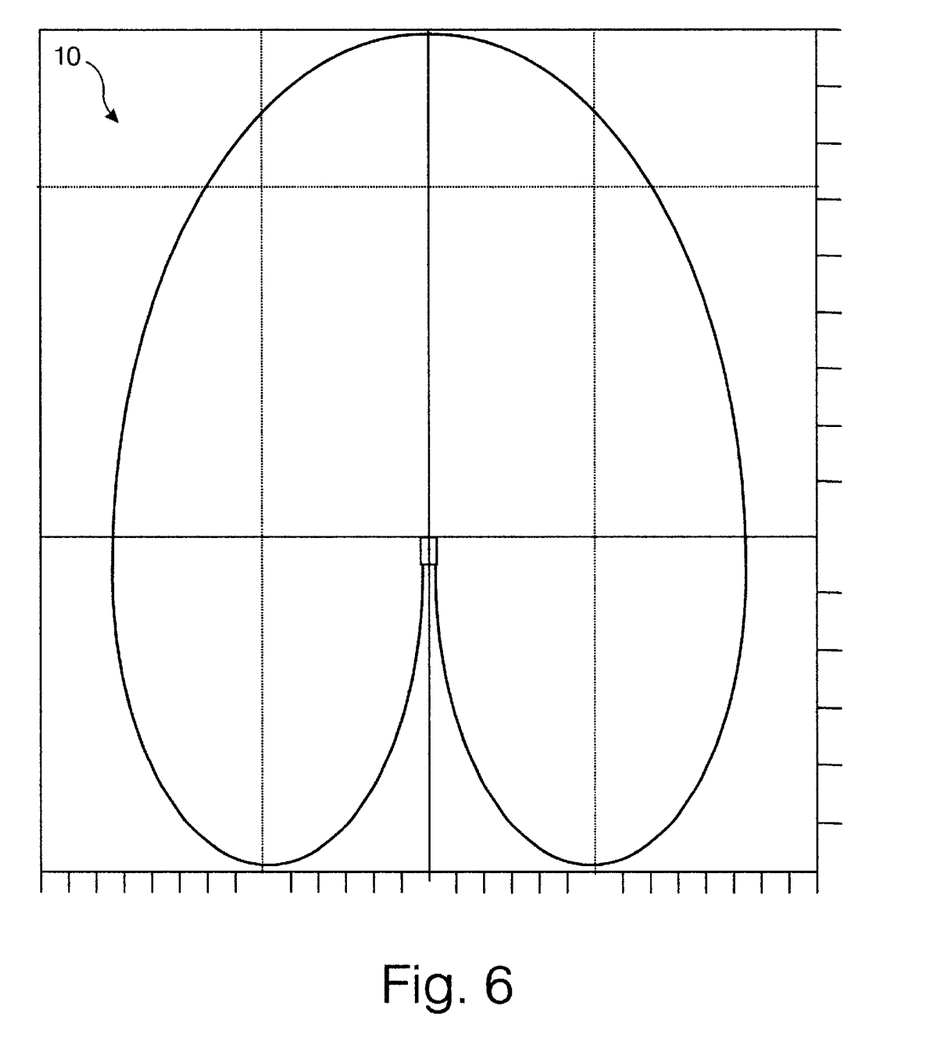
FIG. 6 and 7 show alternative sections for a container of the invention.
Figure 7:
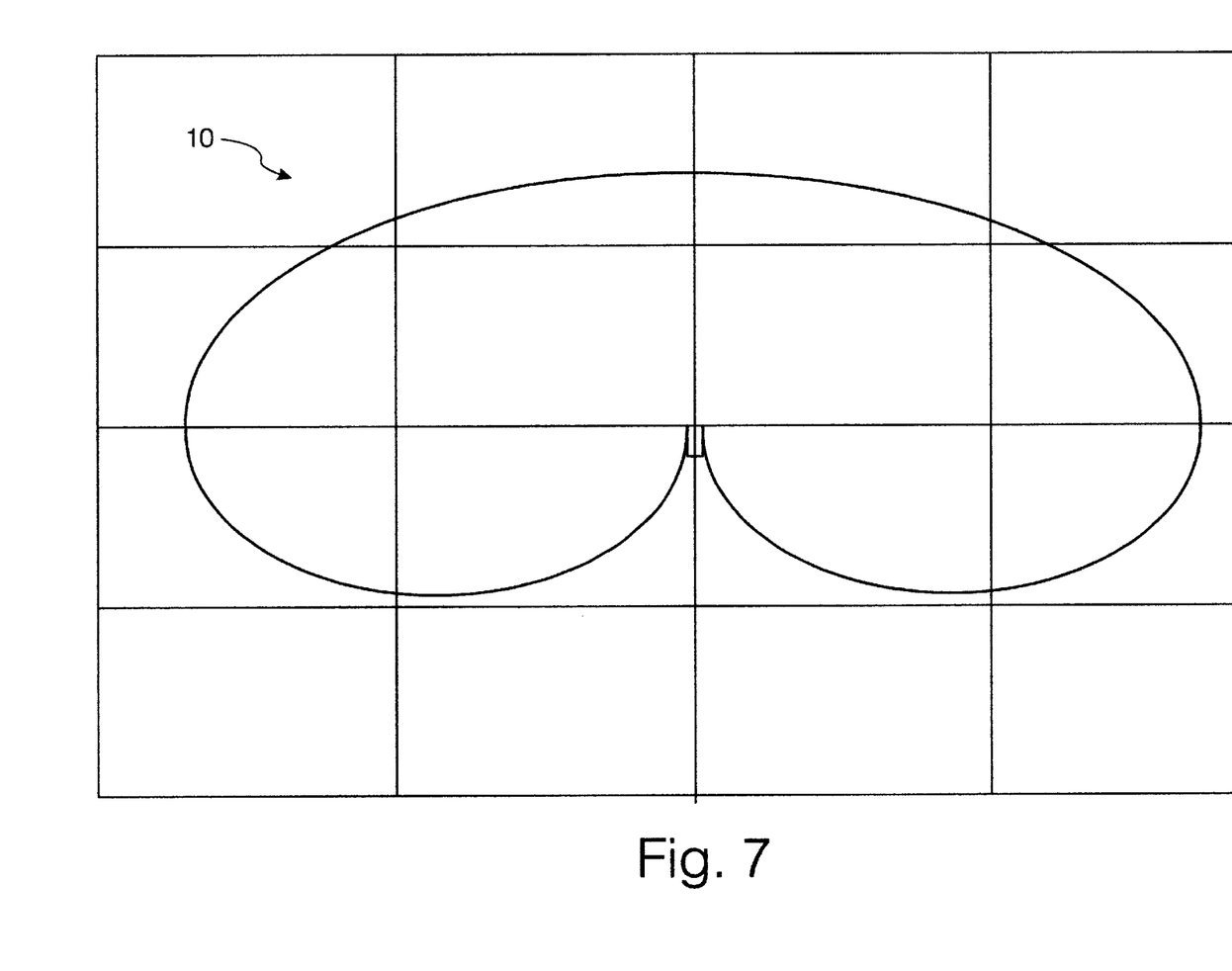

After the peripheral wall 11 has been shaped in the manner explained above, the end walls 12 are sealed to its edges in any suitable manner known in the art. With reference now to FIGS. 5, 6 and 7 these show possible alternative cross-sectional shapes of a container 10 of the invention, the dimensions being given in meters on both the X and Y axes although naturally these dimensions are not limiting of the invention. In each case the generally cardioid shape is maintained so that the flow of liquid within the container follows one of two continuous circulating paths as previously described.

Figure 8:
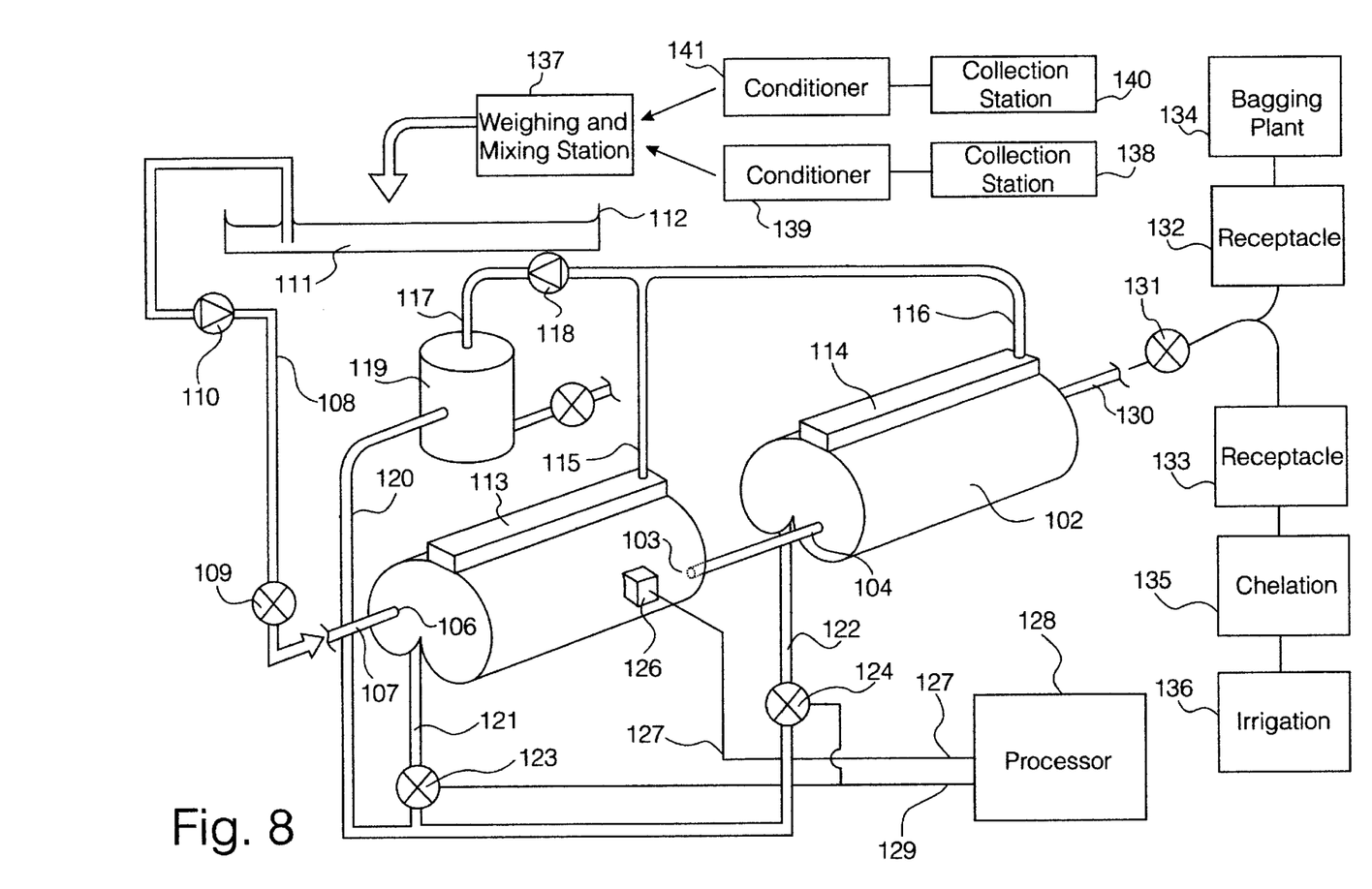
FIG. 8 is a schematic diagram illustrating digester apparatus incorporating the container of the invention.

Referring now to FIG. 8 there is shown, in schematic form, an installation comprising an array of modular containers useful for a slurry digestion process. Although it will be described in relation to this particular application it will be understood that the apparatus may in fact be used for other purposes in which circulatory flow of solids/liquid suspension or mixture is required.

FIG. 8 shows a modular array comprising two tanks or containers 101, 102 each substantially as described hereinbefore with reference to the preceding drawings. The outlet 103 from the container 101 is connected by a tube 104 to the inlet 105 of the tank 102. The tank or container 101 has an inlet 106 to which is connected a pipe 107 fed from a line 108 via a valve 109. A pump 110 draws slurry 111 from an open vessel 112 into which it can be periodically deposited as represented by the arrow A, from which it is drawn by the pump 110 along the line 108 for delivery to the tank 101 as required. The slurry material in the open vessel 112 arrives from a weighing and mixing station 137 as a mixture of solid and liquid organic waste. Solid organic waste is collected at a collection station 138 and, after conditioning in a conditioner 139 supplied to the weighing and mixing station 137. Likewise, liquid waste collected at a collection station 140 and conditioned in a conditioner 141 is supplied to the weighing and mixing station 137 at which the desired ratio of solid and liquid organic wastes is determined for transmission along line A to the open top receptacle 112 for delivery to the container 101.

As can be seen, the inlet 107 to the tank 101 is on the left hand lobe of the cardioid cross-section, whilst the outlet 103 is on the right hand lobe. As the slurry circulates within the tank in the manner described above the material is intermixed at the central median plane and gradually transfers from the left hand chamber to the right hand chamber. The container 102 has its inlet 105 on the right hand lobe and, correspondingly, its outlet on the left hand lobe.

Manifolds 113, 114 collect gas bubbled into the chambers and outlet pipes 115, 116 which join a common line 117 connected by a gas pump 118 to a collector vessel 119 in which the gas is stored under pressure. A first outlet 120 from the pressure vessel 119 leads to delivery pipes 121, 122 leading to the gas inlets of each of the cardioid tanks 101, 102 via valves 123, 124. A second outlet 125 from the pressure vessel 119 leads to a delivery outlet for a consumer or for transport and storage for further use.

A sensor, such as an acoustic transducer 126 in intimate contact with the side wall of one of the containers, in this example the container 101, supplies a signal on a line 127 to an electronic processing circuit 128 indicative of the level of noise within the container. This is compared within the processor 128 with a preset (but adjustable) value representing the minimum level of activity within the container, and processor 128 directs a signal on an output line 129 to the valves 123, 124 to control the amount of gas from the pressure vessel 119 allowed to bubble into the containers 101, 102 to maintain the required minimum level of activity. Should an upper threshold be exceeded, the valves 123, 124 are closed or throttled in order to reduce the flow of gas into the containers 101, 102 thereby minimizing the amount of energy consumption required to maintain the slurry in suspension.

Although a length of pipe 104 is shown connecting the containers 101, 102 these could in fact be directly connected end-to-end in modular fashion to provide an elongate combined container having separate longitudinally divided chambers. This allows, for example, different bacteria to predominate in different chambers so that a wider control on the process can be achieved.

The output gas, typically methane from a slurry digestion process, leaving the pressure vessel 119 may be used for any one of a wide variety of uses such as electricity generation, pumping, process heating, cooling or air conditioning. The slurry after processing leaving the container 102 is fed by a pipe 130 to a separator 131 which separates the solid and liquid components into receptacles 132, 133 respectively. The solid components from the receptacle 132 can then be passed on for composting and treatment and possibly immediate use by being distributed over the ground, or may be bagged up for distribution and sale in a bagging plant 134. The liquid fertilizer in receptacle 133 may be passed on for chelation 135 and thereafter used for example for irrigation, illustrated as step 136.

What is claimed is:

1. A container for a fluid medium, said container having a longitudinal axis and comprising a single side wall and two opposite parallel end walls, said single side wall extending in a continuous curve from a first side wall end to a second side wall end, said first and second side wall ends lying adjacent and spaced from one another and parallel to said longitudinal axis of said container, driving means for driving said fluid medium to circulate around a circulatory path within said container, said single continuously curved side wall of said container defining the outer boundary of said circulatory path, said outer boundary of said circulatory path having an uppermost point and a lowermost point, said two side wall ends of said curved side wall of said container defining a cusp located at a higher point than said lowermost point of said outer boundary of said circulatory path, said driving means comprising an elongate duct lying between said two side wall ends of said single continuously curved side wall of said container, a plurality of orifices in said elongate duct wherein when a gas is introduced under pressure into said duct the gas leaves said orifices and rises through said fluid as bubbles to drive the circulation of fluid within said container as said bubbles rise through said fluid, said bubbles defining a substantially vertical longitudinal median plane of said container, fluid inlet means in one said end wall at one end of said container, fluid outlet means in the other said end wall at the opposite end of said container, said fluid outlet and said fluid inlet being on opposite sides of said vertical longitudinal median plane defined by said bubbles.

2. The container according to claim 1, having means for maintaining solids in suspension in a liquid by causing forced circulation thereof with the container stationary, wherein an upper part of the container wall is so shaped as to guide the circulatory motion of the fluid to follow a downwardly curved path (32) so as to maintain the solids in suspension.

3. An installation comprising a plurality of containers according to any of according to claim 1, in an arrangement with means (104) interconnecting the outlet of one container to an inlet of a successive container (102).

4. The container of claim 1 wherein the container has a vertical section which is symmetrically bilobate with a single cusp separating the lobes.

5. The container of claim 1 wherein the vertical section of the container has a generally cardioid form.

6. A container for a fluid medium, said container having a longitudinal axis and comprising a single side wall and two opposite parallel end walls, said single side wall extending in a continuous curve from a first side wall end to a second side wall end, said first and second side wall ends lying adjacent and spaced from one another and parallel to said longitudinal axis of said container, driving means for driving said fluid medium to circulate around a circulatory path within said container, said single continuously curved side wall of said container defining the outer boundary of said circulatory path, said outer boundary of said circulatory path having an uppermost point and a lowermost point, said two side wall ends of said curved side wall of said container defining a cusp located at a higher point than said lowermost point of said outer boundary of said circulatory path, said driving means comprising an elongate duct lying between said two side wall ends of said single continuously curved side wall of said container, a plurality of orifices in said elongate duct wherein when a gas is introduced under pressure into said duct the gas leaves said orifices and rises through said fluid as bubbles to drive the circulation of fluid within said container as said bubbles rise through said fluid, said bubbles defining a substantially vertical longitudinal median plane of said container.

7. A method of maintaining a fluid suspension within a container by creating a circulatory motion of fluid within the container by a fluid driving means acting to introduce gas under pressure to form a curtain of bubbles to cause the fluid to move within the container, the fluid driving means being located at a height within the container spaced above a lowermost point of the circulatory motion and comprising a gas introduced into the interior of the container that bubbles up through the suspension, the fluid flow is constrained to follow a continuously curving path by the shape of the container wall with no discontinuities from an upper part of the container to the part at which the gas is introduced and said fluid flow is guided within the container in a smoothly continuous curve from the lowermost point to the driving means by flow guide surfaces forming part of the outer wall of the container and defining part of the continuously curving path with the container, the entirety of the continuously curving path within the container being defined by the outer wall of the container, the suspension being caused to flow through the container from one end to the other, and being caused to traverse across the curtain of bubbles at least once in its path from an inlet to an outlet of the container.

* * * * *